(12) United States Patent
Burns et al.

(10) Patent No.: US 8,707,549 B2
(45) Date of Patent: Apr. 29, 2014

(54) ERGONOMIC GRIP ASSEMBLIES AND HANDLES FOR ULTRASOUND TRANSDUCERS

(75) Inventors: Joie Burns, Boise, ID (US); Michelle Sabick, Boise, ID (US); Seth Kuhlman, Mesa, AZ (US); Carly Lockard, Boise, ID (US); Brittany Siewert, Bend, OR (US)

(73) Assignee: Boise State University, Boise, ID (US)

( * ) Notice: Subject to any disclaimer, the term of this patent is extended or adjusted under 35 U.S.C. 154(b) by 122 days.

(21) Appl. No.: 13/442,593

(22) Filed: Apr. 9, 2012

(65) Prior Publication Data

US 2013/0263438 A1 Oct. 10, 2013

(51) Int. Cl.
*B23P 21/00* (2006.01)
*B23Q 15/00* (2006.01)

(52) U.S. Cl.
USPC .................. 29/721; 29/729; 29/760; 29/761; 29/764; 310/326; 310/327; 310/333; 310/357; 310/367; 16/422; 347/68; 347/69; 347/70; 347/71; 347/72

(58) Field of Classification Search
USPC .............. 29/721, 729, 760, 761, 764; 16/422; 310/326, 327, 333–337, 357, 367; 347/54, 68, 69, 70, 71, 72
See application file for complete search history.

(56) References Cited

U.S. PATENT DOCUMENTS

| | | | |
|---|---|---|---|
| 4,920,966 A * | 5/1990 | Hon et al. | 600/459 |
| 5,897,503 A | 4/1999 | Lyon et al. | |
| 6,237,192 B1 | 5/2001 | Garrison et al. | |
| 2003/0060714 A1 | 3/2003 | Henderson et al. | |
| 2008/0064960 A1 * | 3/2008 | Whitmore et al. | 600/459 |

* cited by examiner

*Primary Examiner* — Paul D Kim
(74) *Attorney, Agent, or Firm* — McKee, Voorhees & Sease, P.L.C.

(57) ABSTRACT

The present invention relates to ultrasound transducers for ultrasonic imaging systems and, in particular, to improved grip assemblies for ultrasound transducers. One grip assembly includes a locking plate defining first and second apertures and a coupling post extending from the locking plate. An interface plate has a first elongate extension being extendable at least partially through the first aperture and a second elongate extension being extendable at least partially through the second aperture. A handle is coupled to the locking plate and includes a grip, a coupling interface, and a neck extending between the grip and the coupling interface. The coupling interface defines a coupling aperture for receiving the coupling post.

14 Claims, 4 Drawing Sheets

ERGONOMIC GRIP ASSEMBLIES AND HANDLES FOR ULTRASOUND TRANSDUCERS

BACKGROUND

The present invention relates to ultrasound transducers for ultrasonic imaging systems and, in particular, to improved handles for ultrasound transducers.

Medical sonography covers a broad spectrum of specialty areas including vascular, cardiac, and general (e.g., abdominal, superficial parts, gynecologic and obstetric) sonography. Because medical sonography covers such a broad array of clinical needs without the use of ionizing radiation, it has become essential in the diagnosis of many life-threatening diseases.

Though sonography is an indispensable tool, it is not without its shortcomings. For example, each year more than 80% of clinical sonographers experience musculoskeletal related pain, with up to 20% of these sonographers suffering career-ending injuries. Current research points to the poor ergonomics of ultrasound probes or transducers as a main factor in causing these work-related musculoskeletal disorders. Specifically, work-related musculoskeletal disorders of the hand and wrist have been linked to grip effort and wrist range of motion for those using ultrasound transducers. In tests undertaken to pinpoint the cause of these hand and wrist musculoskeletal disorders, muscle activation was quantified as an indirect measure of the grip effort required by the sonographer to perform a scan with the ultrasound transducer.

Accordingly, there is a need for a more ergonomic gripping assembly interface between the sonographer and ultrasound transducer in order to reduce work-related musculoskeletal disorders.

SUMMARY OF THE INVENTION

The present invention relates to ultrasound transducers for ultrasonic imaging systems and, in particular, to improved handles for ultrasound transducers.

In some aspects of the disclosure, a grip assembly is disclosed. The grip assembly may include a locking plate defining first and second apertures and a coupling post extending from the locking plate. The grip assembly may also include an interface plate having a first elongate extension being extendable at least partially through the first aperture and coupled thereto and a second elongate extension being extendable at least partially through the second aperture and coupled thereto. The grip assembly may further include a handle having a grip, a coupling interface, and a neck extending between the grip and the coupling interface. The coupling interface may define a coupling aperture configured to receive the coupling post, whereby the handle is coupled to the locking plate.

In some aspects of the disclosure, a method of customizing a transducer is disclosed. The method may include arranging a universal clamp about the transducer. The universal clamp may include a locking plate that defines first and second apertures and a coupling post extending from the locking plate. The universal clamp may also include an interface plate having first and second elongate extensions extending therefrom. The method may also include extending the first and second elongate extensions though the first and second apertures, respectively, and securing the first and second elongate extensions to the locking plate as extended through the first and second apertures, whereby the universal clamp is coupled to the transducer. The method may further include coupling a handle to the locking plate. The handle may have a grip, a coupling interface, and a neck extending between the grip and the coupling interface. The coupling interface may define a coupling aperture for receiving the coupling post, whereby the handle is coupled to the locking plate.

In some aspects of the disclosure, another grip assembly is disclosed. The grip assembly may include a universal clamp including a slotted locking plate and an interface plate. The slotted locking plate may define first and second slots and the interface plate may have a first elongate extension being extendable at least partially through the first slot and a second elongate extension being extendable at least partially through the second slot. The grip assembly also includes first and second locking mechanisms movably disposed within the locking plate and configured to lock the first and second elongate extensions within the first and second apertures, respectively. The grip assembly may further include a coupling post extending from the locking plate, and a handle having a grip and a coupling interface defining a coupling aperture for receiving the coupling post. The coupling interface may be configured to couple the handle to the universal clamp.

The features and advantages of the present invention will be readily apparent to those skilled in the art upon a reading of the description of the preferred embodiments that follows.

BRIEF DESCRIPTION OF THE DRAWINGS

The following figures are included to illustrate certain aspects of the present invention, and should not be viewed as exclusive embodiments. The subject matter disclosed is capable of considerable modifications, alterations, combinations, and equivalents in form and function, as will occur to those skilled in the art and having the benefit of this disclosure.

DETAILED DESCRIPTION

The present invention relates to ultrasound transducers for ultrasonic imaging systems and, in particular, to improved handles and gripping assemblies for ultrasound transducers.

The exemplary gripping assemblies disclosed herein have been ergonomically designed so as to reduce the incidence of work-related musculoskeletal disorders often suffered by sonographers in recording ultrasound images. The gripping assemblies are designed to be ergonomically superior to traditional ultrasound transducer handles and gripping assemblies in that the required gripping force to hold onto or otherwise manipulate the ultrasound transducer is dramatically reduced. The gripping assemblies disclosed herein increase gripping comfort for the user and thereby decrease the risk of work-related musculoskeletal injury. Moreover, the disclosed gripping assemblies are specifically designed to be coupled to a wide range of sizes and shapes of commercially-available ultrasound transducers. Consequently, no modification to currently-used ultrasound transducers is required by using the disclosed gripping assemblies.

Figure 1A:
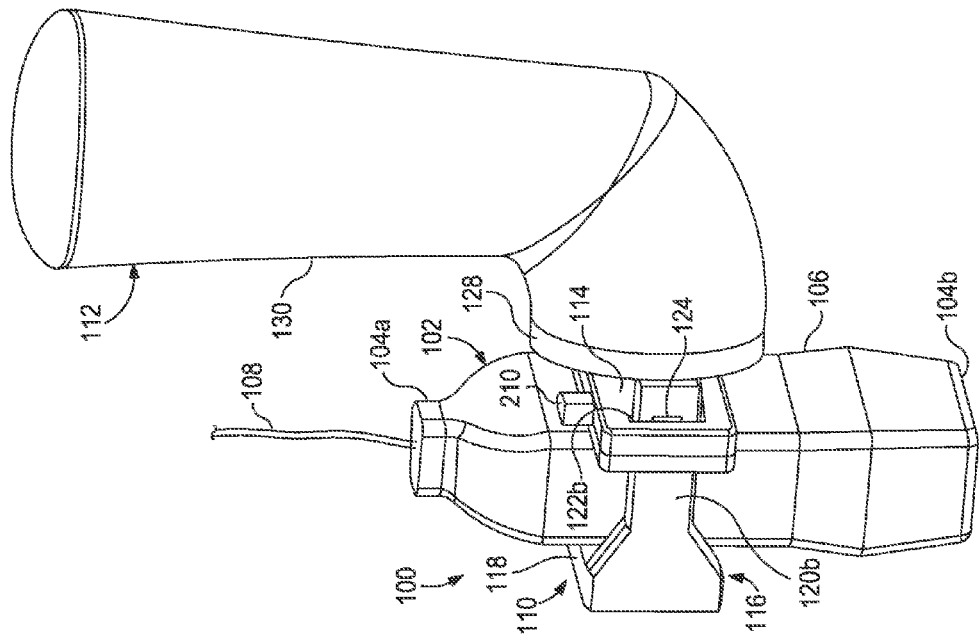
FIGS. 1a and 1b illustrate opposing isometric views of an exemplary grip assembly as coupled to a transducer, according to one or more embodiments.
Figure 1B:
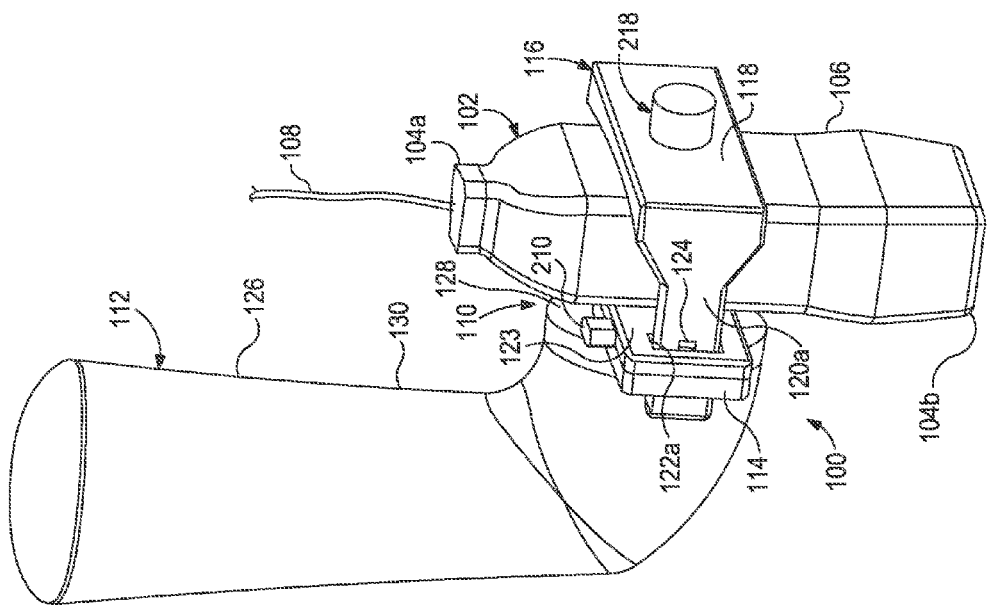
Figure 1C:
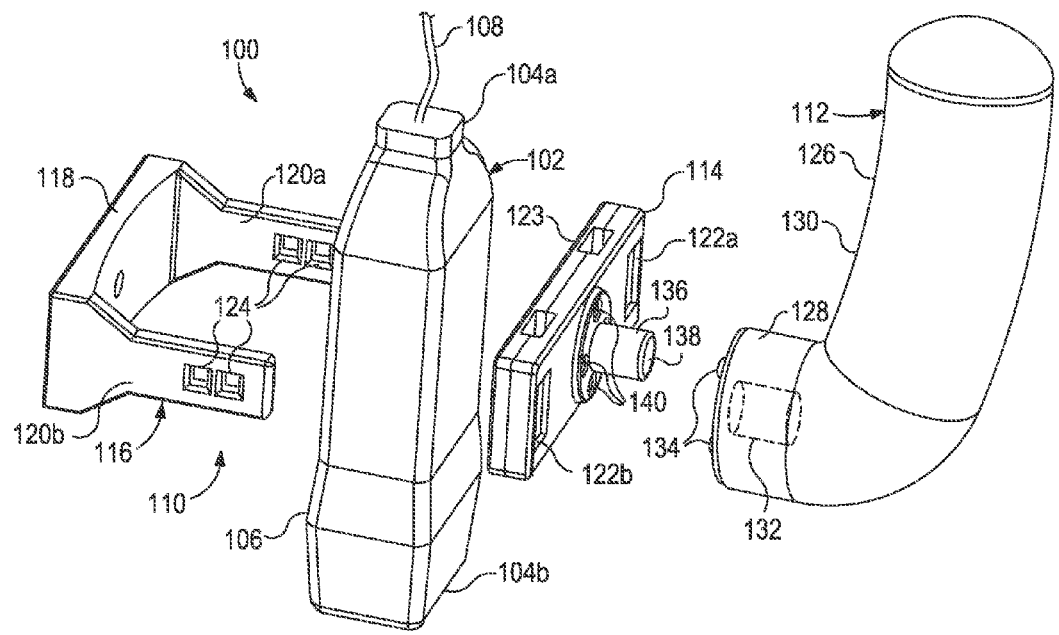
FIG. 1c illustrates an exploded view of the grip assembly and transducer shown in FIGS. 1a and 1b, according to one or more embodiments.

Referring to FIGS. 1a, 1b, and 1c, illustrated is an exemplary grip assembly 100 used in conjunction with an ultrasound transducer 102, according to one or more embodiments. Specifically, FIGS. 1a and 1b illustrate front and back isometric views, respectively, of the grip assembly 100 as coupled or otherwise attached to the transducer 102, and FIG. 1c provides an exploded view of the same. The depicted transducer 102 may be any one of a variety of commercially-available ultrasound transducers such as, but not limited to, a sector phased array, a convex array, a microconvex array, a linear array, or a matrix array. The transducer 102 is an elongated device having a proximal end 104a and a distal end 104b and an external casing 106 that is usually grasped by a sonographer or other user. The casing 106 houses well-known internal components. For example, the distal end 104b may house a transducer array (not shown) which is generally placed against a patient's body to obtain ultrasound images. Attached to the proximal end 104a of the transducer 102 is a cord 108 which provides power to the transducer 102 and otherwise carries data signals between the transducer 102 and an adjacent ultrasound imaging system (not shown). As discussed in greater detail below, the grip assembly 100 is able to be coupled to a wide range of sizes and designs of transducers 102 and provides a user with an ergonomic means of manipulating the transducer 102 so as to reduce work-related musculoskeletal disorders.

The grip assembly 100 may include at least a universal clamp 110 and a handle 112. The universal clamp 110 may include a slotted locking plate 114 and a slide lock U-channel 116, where the slide lock U-channel 116 is configured to engage and be locked at least partially within the slotted locking plate 114 during use. FIGS. 1a and 1b illustrate the universal clamp 110 in a "locked" configuration, where the universal clamp 110 engages or is otherwise coupled to the transducer 102 such that relative movement between the two is substantially prevented. FIG. 1c illustrates the universal clamp 110 in a disengaged configuration, where the slotted locking plate 114 and slide lock U-channel 116 are disengaged and therefore the transducer 102 is free to move.

The slide lock U-channel 116 may include an interface plate 118 and a pair of laterally-offset, elongate extensions 120a and 120b extending longitudinally from the interface plate 118. When properly coupled to the transducer 102, the interface plate 118 may be configured to engage or otherwise be arranged substantially adjacent the casing 106 of the transducer 102. In one or more embodiments, the interface plate 118 may have a layer of gripping material (not shown) applied to its inner surface in order to provide increased frictional engagement with the transducer 102 during use. In at least one embodiment, the gripping material may be a thin layer of silicone rubber or another type of elastomer. In other embodiments, however, the gripping material may be made of other pliant or otherwise tacky materials such as, but not limited to, polymers, plastics, foams, combinations thereof, or the like. In yet other embodiments, the gripping material may be a textured surface made of, for example, any tacky or soft material.

To couple the slotted locking plate 114 to the slide lock U-channel 116, each elongate extension 120a,b may be configured to extend longitudinally through corresponding apertures or slots 122a and 122b, respectively, defined in the slotted locking plate 114. Specifically, the first elongate extension 120a may be configured to extend through the first slot 122a, and the second elongate extension 120b may be configured to extend through the second slot 122b. Each elongate extension 120a,b may further define one or more apertures 124 along their respective axial lengths. As will be described in more detail below, the apertures 124 may at least partially facilitate the locking engagement between the slotted locking plate 114 and the slide lock U-channel 116. In at least one embodiment, a back portion 123 of the slotted locking plate 114 may also have a layer of gripping material (not shown) applied thereto, similar to the gripping material applied to the inner surface of the interface plate 118, in order to provide increased frictional engagement with the transducer 102 once the slotted locking plate 114 is appropriately coupled to the slide lock U-channel 116.

The handle 112 may include a grip 126, a coupling interface 128, and a neck 130 that extends therebetween. The grip 126 may provide the user with a power or palmar gripping location, as opposed to a pinch grip which can accelerate musculoskeletal injury to the hand and wrist. The grip 126 may further provide a compliant surface configured to evenly distribute hand pressure when applied thereto. In one or more embodiments, the grip 126 may be coated with a gripping material, such as silicone rubber, in order to provide the user with increased grippability when manipulating the position of the transducer 102. In other embodiments, the grip 126 may be knurled in order to provide a more grippable surface. As will be discussed in more detail below, several other grip 126 designs are possible, thereby providing the user with a choice of grips 126 that may be selected based on individualized comfort preferences or grips 126 specifically designed for the type of scan being taken.

Referring specifically to FIG. 1c, the coupling interface 128 may define a coupling aperture 132 that extends a short distance into the coupling interface 128 and one or more indexing protrusions 134 (two shown) that extend axially from the coupling interface 128. To couple the handle 112 to the universal clamp 110, the coupling aperture 132 may be configured to be seated on or otherwise receive a corresponding coupling post 136 extending from the slotted locking plate 114. In one embodiment, a magnet 138 may be arranged on the coupling post 136 and configured to magnetically-attract another magnet (not shown) arranged within the coupling aperture 132, and thereby couple the handle 112 to the universal clamp 110 via magnetic engagement. In other embodiments, the magnet 138 may be configured to magnetically-attract a metallic portion of the coupling aperture 132 or handle 112, such as a washer or the like embedded within the coupling aperture 132. In yet other embodiments, the magnet 138 may be arranged within the coupling aperture 132 and configured to magnetically-attract the coupling post 136. In yet further embodiments, the handle 112 may be coupled to the universal clamp 110 by first inserting the coupling post 136 into the coupling aperture 132 and then mechanically fastening the handle 112 to the universal clamp 110, such as through the use of a set screw (not shown) or the like configured to engage the coupling post 136 and prevent its removal from the coupling aperture 132. In yet further embodiments, the coupling post 136 may be threaded into the coupling aperture 132.

As another step of coupling the handle 112 to the universal clamp 110, the one or more indexing protrusions 134 may be configured to be received in a corresponding one or more indexing holes 140 (three shown in FIG. 1c) defined in the slotted locking plate 114 about the coupling post 136. As illustrated, the indexing holes 140 may be circumferentially offset from each other at 90° intervals. Accordingly, the handle 112 may be able to be radially indexed about the coupling post 136 at 90° intervals by locating and aligning the indexing protrusions 134 with the corresponding indexing holes 140. Those skilled in the art will readily appreciate the advantages this provides to the user. For example, some ultrasound applications require the sonographer to operate the transducer 102 in awkward configurations which can place significant strain on the wrist and fingers of the sonographer. Being able to releasably engage the handle 112 quickly from the universal clamp 110 and radially index the handle 112 to a new radial position provides a significant advantage in allowing the sonographer to maintain the required pressure on the transducer 102, but at a more comfortable angle for the wrist and fingers. Those skilled in the art will also readily recognize that the indexing holes 140 may be circumferentially offset from each other at intervals greater than or less than 90°, without departing from the scope of the disclosure.

Figure 2:
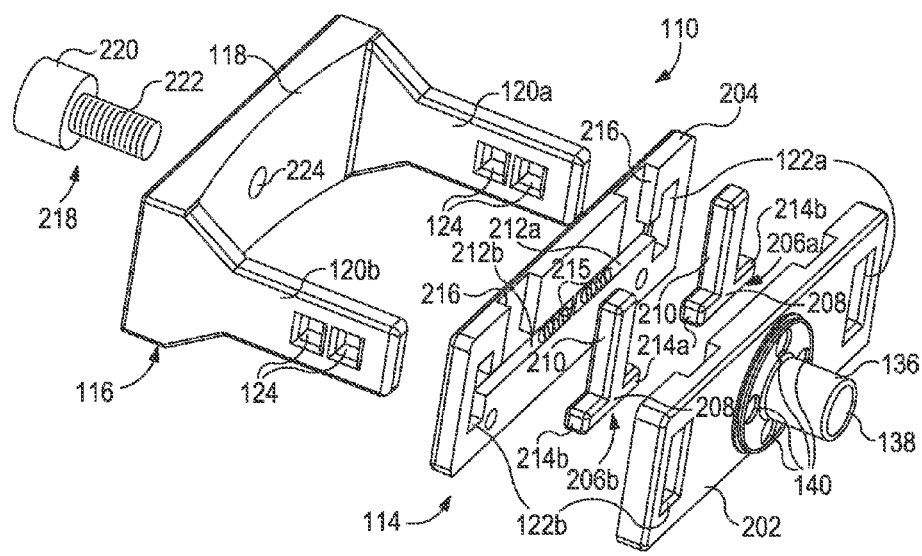
FIG. 2 illustrates an exploded view of an exemplary universal clamp, according to one or more embodiments.

Referring now to FIG. 2, with continued reference to FIGS. 1a-1c, illustrated is an exploded view of the universal clamp 110, according to one or more embodiments. As depicted, the slotted locking plate 114 may be separated into or otherwise include at least a handle mating portion 202 and a transducer mating portion 204. The handle and transducer mating portions 202, 204 may be configured to be coupled together so as to form the slotted locking plate 114 and cooperatively define the first and second slots 122a,b. In one embodiment, the portions 202, 204 are coupled together using an adhesive. In other embodiments, however, the portions 202, 204 may be coupled together using, for example, mechanical fasteners, welding or brazing techniques, clips, combinations thereof, or the like.

One or more locking mechanisms 206 (shown as a first locking mechanism 206a and a second locking mechanism 206b) may be movably disposed within the locking plate 114 and configured to lock the first and second elongate extensions 120a,b within the corresponding first and second slots 122a,b, respectively. In one or more embodiments, each locking mechanism 206a,b may include a base portion 208 and a stem 210 extending from the base portion 208. Each base portion 208 may be arranged within a corresponding lateral groove 212a and 212b defined within the universal clamp 110. In some embodiments, the lateral grooves 212a,b may be cooperatively defined by both the handle mating portion 202 and the transducer mating portion 204. In other embodiments, however, the lateral grooves 212a,b may be defined solely by one or the other of the handle mating portion 202 and the transducer mating portion 204.

Each base portion 208 may include a biasing end 214a and a locking end 214b. The biasing ends 214a may each be configured to bias a spring or other compliant member 215 arranged within the respective lateral groove 212a,b and configured to bias the corresponding locking mechanism 206a,b toward its adjacent slot 122a,b. With the elongate extensions 120a,b extended through the corresponding slots 122a,b, the locking ends 214b may be configured to extend through a corresponding one of the apertures 124, thereby locking the respective elongate extension 120a,b such that removal from the locking plate 114 is generally prevented.

The stem 210 of each locking mechanism 206a,b may extend through a corresponding slip aperture 216 defined within the locking plate 114. In some embodiments, the slip apertures 216 may be cooperatively defined by both the handle mating portion 202 and the transducer mating portion 204. In other embodiments, however, the slip apertures 216 may be defined solely by one or the other of the handle mating portion 202 and the transducer mating portion 204. Each stem 210 may be configured to extend through its corresponding slip aperture 216 such that the locking mechanism 206a,b can be manually manipulated by the user. This can be seen in FIGS. 1a and 1b, where the stem(s) 210 is shown protruding out of the locking plate 114.

Moreover, each slip aperture 216 may be sufficiently wide so as to allow the corresponding stem 210 to be laterally shifted by the user such that the user is able to retract the base 208 against the biasing force of the spring 215. As the base 208 is forced against the spring 215 the locking end 214b is generally removed from the area of the corresponding slot 122a,b, thereby either allowing the corresponding elongate extension 120a,b to enter the respective slot 122a,b, or otherwise disengaging the corresponding elongate extension 120a,b from its locked configuration where the locking end 214b is inserted into one of the apertures 124.

While only two apertures 124 are depicted as being defined on each elongate extension 120a,b, it will be appreciated that any number of apertures 124 may be employed, without departing from the scope of the disclosure. Consequently, the elongate extensions 120a,b may be extended through its corresponding slot 122a,b to a greater or lesser degree, in order to adequately couple the universal clamp 110 to the transducer 102 (FIGS. 1a and 1b). This may prove advantageous in allowing the universal clamp 110 to be coupled to transducers 102 exhibiting a wide range of sizes and designs.

In one or more embodiments, the universal clamp 110 may further include an adjustment screw 218 having a head 220 and a threaded stem 222 extending therefrom. The threaded stem 222 may be configured to threadably engage or otherwise be extended through an adjustment aperture 224 defined in the interface plate 118. In operation, once the universal clamp 110 is coupled to the transducer 102, as shown in FIGS. 1a and 1b, the adjustment screw 218 may be threaded into the adjustment aperture 224 and extended until the threaded stem 222 contacts the casing 106 of the transducer 102. Further tightening or advancement of the adjustment screw 218 may bias against the casing 106 and serve to finely adjust the position of the transducer 102 with respect to the interface plate 118. This may prove advantageous in providing a more secure coupling of the universal clamp 110 to the transducer 102, especially in instances where there may remain a small amount of play between the universal clamp 110 and the transducer 102 resulting from the predetermined spaced apertures 124 not fully aligning with the particular depth or size of the transducer 102 being coupled to.

Figure 3A:
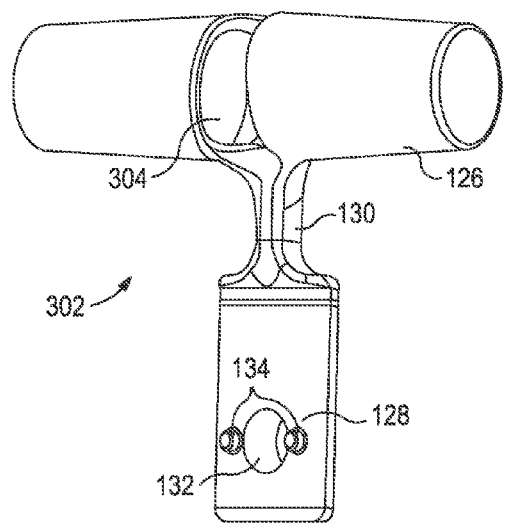
FIGS. 3a and 3b illustrate an exemplary handle, according to one or more embodiments.
Figure 3B:
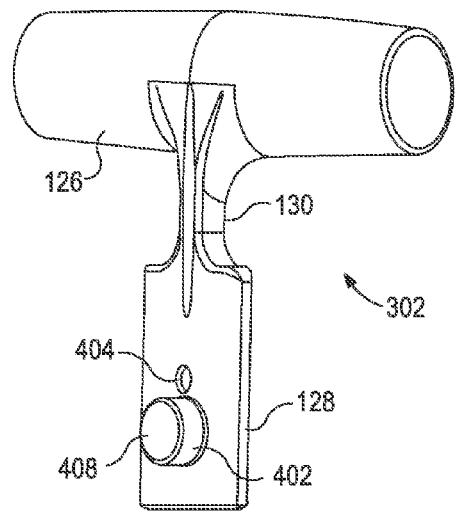

Referring now to FIGS. 3a and 3b, with continued reference to FIGS. 1a-1c and FIG. 2, illustrated is another exemplary handle 302, according to one or more embodiments. The handle 302 may be used in conjunction with the grip assembly 100 described above, but used in place of the handle 112. Accordingly, the handle 302 may be best understood with reference to the discussion above regarding the handle 112, where like numerals represent like elements that will not be described again in detail. As illustrated, the handle 302, which may generally provide the user with a T-shaped gripping interface, may include the grip 126, the coupling interface 128, and the neck 130 that extends therebetween. Again, the grip 126 may provide the user with a palmar gripping location and a compliant surface configured to evenly distribute hand pressure when applied thereto. The grip 126 may further define a channel 304 which may accommodate the cord 108 (FIGS. 1a-1c) as extending from the proximal end 104a of the transducer 102.

As with the handle 112 described above, the coupling interface 128 shown in FIGS. 3a and 3b may define a coupling aperture 132 that extends a short distance into the coupling interface 128 and one or more indexing protrusions 134 (two shown) extending axially from the coupling interface 128. To couple the handle 302 to the universal clamp 110, the coupling aperture 132 may be seated on or otherwise receive the corresponding coupling post 136 (FIG. 1c) extending from the slotted locking plate 114. Accordingly, the combination of the coupling aperture 132 and coupling post 136 provides axial stability to the handle 302 as the user manipulates the position of the transducer 102.

Moreover, the one or more indexing protrusions 134 may be configured to be received in the corresponding one or more indexing holes 140 (FIG. 1c) defined in the slotted locking plate 114. Again, the handle 302 may be radially indexed about the coupling post 136 at various radial intervals (e.g., 90°) by locating and aligning corresponding indexing holes 140 on the slotted locking plate 114 with the indexing protrusions 134. Accordingly, the combination of the indexing protrusions 134 and the corresponding indexing holes 140 provides radial stability to the handle 302 as the user manipulates the position of the transducer 102.

Figure 4A:
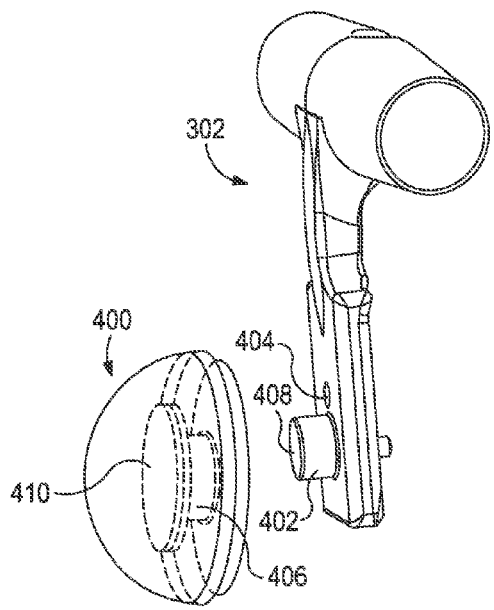
FIGS. 4a and 4b illustrate an exemplary attachment device as releasably coupled to the handle of FIGS. 3a and 3b, according to one or more embodiments.
Figure 4B:
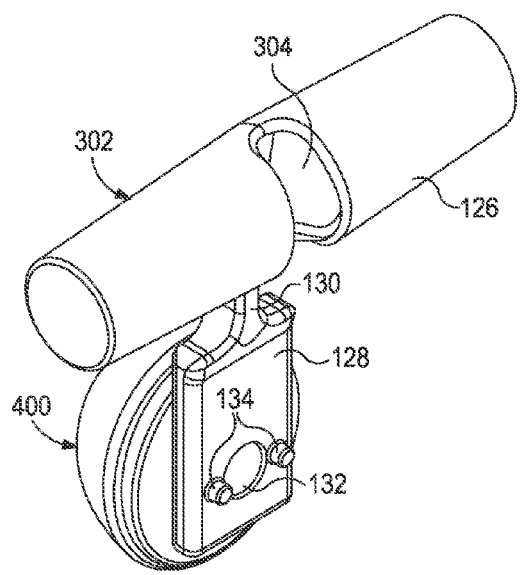

Referring now to FIGS. 4a and 4b, with continued reference to FIGS. 3a and 3b, illustrated is an exemplary attachment device 400 that may be coupled to the handle 302, according to one or more embodiments. The attachment device 400 may be coupled to the handle 302 to provide the user with an additional gripping or palmar interface to further manipulate the position of the transducer 102 (FIGS. 1a-1c). Specifically, the attachment device 400 provides a gripping location that is closer to the base of the transducer 102, thereby providing the user with increased leverage. Accordingly, the user may be able to grip one or both of the handle 302 and the attachment device 400 during use. As depicted, the attachment device 400 may provide a generally hemispherical structure configured to generally accommodate the palm of a user's hand. The hemispherical geometry may prove advantageous in providing the user with a variety of gripping styles, thereby again enhancing leverage on the transducer 102. In other embodiments, however, the attachment device 400 may be defined by other geometrical configurations, without departing from the scope of the disclosure. The outer surface of the attachment device 400 may include a layer of gripping material, such as silicone rubber, a texture, or the like, in order to increase grippability and comfort.

In some embodiments, the coupling interface 128 of the handle 302 may further define an attachment post 402 and one or more attachment apertures 404 (one shown). The attachment post 402 may be configured to extend longitudinally from the back side of the coupling interface 128. In at least one embodiment, the attachment post 402 may form the outer structure for at least a portion of the coupling aperture 132 as it extends through the coupling interface 128. The attachment device 400 may define an attachment device aperture 406 configured to mate with or otherwise receive the attachment post 402.

To couple the attachment device 400 to the handle 302, the attachment device aperture 406 may be seated on or otherwise receive the corresponding attachment post 402 extending from the coupling interface 128. In one embodiment, the attachment post 402 may include a magnet 408 arranged thereon or otherwise forming an integral part thereof, the magnet 408 being configured to magnetically-attract another magnet 410 arranged within the attachment device aperture 406, and thereby couple the attachment device 400 to the handle 302 via magnetic engagement. In other embodiments, however, the magnet 408 may be configured to magnetically-attract a metallic portion of the attachment device aperture 406 or attachment device 400, such as a washer or the like embedded within the attachment device aperture 406. In yet other embodiments, the second magnet 410 arranged within the attachment aperture 406 may be configured to magnetically-attract the attachment post 402. In yet further embodiments, the attachment device 400 may be coupled to the handle 302 using one or more mechanical fasteners, such a set screw (not shown) or the like, as generally described above.

The attachment apertures 404 may be defined in the back side of the coupling interface 128. While only one attachment aperture 404 is depicted in FIGS. 3b and 4a, it will be appreciated that any number of attachment apertures may be employed without departing from the scope of the disclosure. One or more attachment device protrusions (not shown) may extend from the attachment device 400 and may be configured to mate with the attachment apertures 404. Specifically, the attachment device protrusions may be configured to be received in the corresponding one or more attachment apertures 404 defined in the coupling interface 128. The combination of the attachment aperture 406 and the attachment post 402 provides axial stability to the attachment device 400 as the user manipulates the position of the transducer 102. The combination of the attachment device protrusion(s) and the attachment aperture(s) 404, on the other hand, provides radial stability to the attachment device 400 as the user manipulates the position of the transducer 102.

Figure 5A:
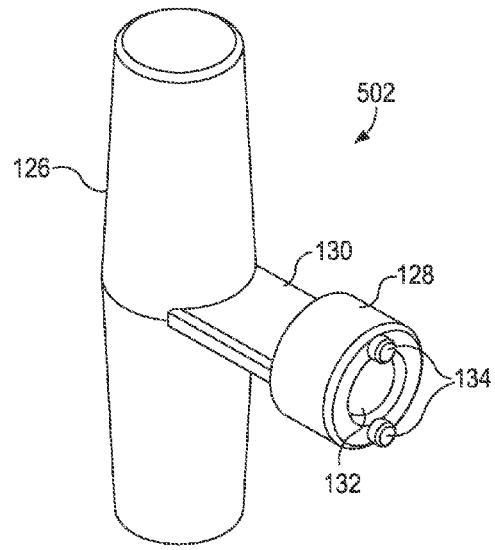
FIGS. 5a and 5b illustrate another exemplary handle, according to one or more embodiments.
Figure 5B:
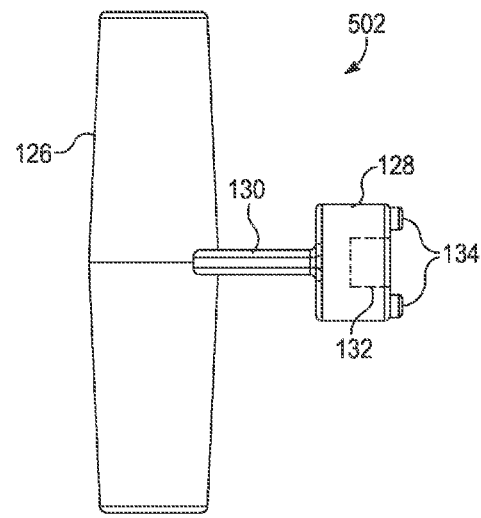

Referring now to FIGS. 5a and 5b, with continued reference to FIGS. 1a-1c and FIG. 2, illustrated is another exemplary handle 502, according to one or more embodiments. Specifically, FIG. 5a provides an isometric view of the handle 500 and FIG. 5b provides a side view thereof. The handle 502 may be used in conjunction with the grip assembly 100 described above, but be used in place of the handle 112. Accordingly, the handle 502 may be best understood with reference to the discussion above regarding the handles 112 and 302, where like numerals represent like elements that will not be described again in detail. Similar to the handle 302 described above with reference to FIGS. 3a and 3b, the handle 502 may generally provide the user with a T-shaped gripping interface and may include the grip 126, the coupling interface 128, and the neck 130 that extends therebetween. Again, the grip 126 may provide the user with a power or palmar gripping location and a compliant surface configured to evenly distribute hand pressure when applied thereto.

Unlike the handle 302 described above in FIGS. 3a and 3b which provides a generally vertical gripping interface, the handle 502 provides the user with a generally horizontal or axial gripping interface. As with previous embodiments, the handle 502 may be coupled to the universal clamp 110 (FIGS. 1a-1c and FIG. 2) by mating the coupling aperture 132 with the corresponding coupling post 136 (FIG. 1c) extending from the slotted locking plate 114. Moreover, the one or more indexing protrusions 134 (two shown) may mate with the corresponding one or more indexing holes 140 (FIG. 1c) defined in the slotted locking plate 114, and the handle 502 may be radially indexed about the coupling post 136 at various radial intervals (e.g., 90°) by locating and aligning corresponding indexing holes 140 with the indexing protrusions 134. Accordingly, the combination of the coupling aperture 132 and coupling post 136 provides axial stability to the handle 502 and the combination of the indexing protrusions 134 and the corresponding indexing holes 140 provides radial stability to the handle 502 as the user manipulates the position of the transducer 102.

Figure 6:
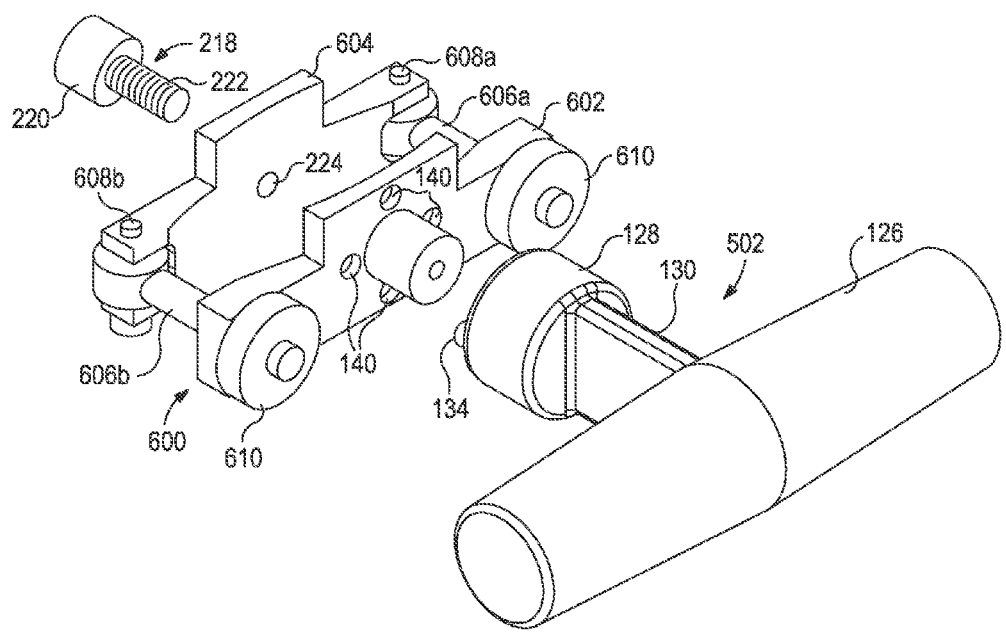
FIG. 6 illustrates another exemplary universal clamp in conjunction with the handle of FIGS. 5a and 5b, according to one or more embodiments.

Referring now to FIG. 6, illustrated is another exemplary universal clamp 600, according to one or more embodiments. The universal clamp 600 may be similar in some respects to the universal clamp 110 described above with reference to FIGS. 1a-1c and FIG. 2 and therefore may be best understood with reference thereto, where like numerals indicate like elements that will not be described in detail. FIG. 6 depicts the universal clamp 600 as being attachable to the handle 502, as described in FIGS. 5a and 5b. Those skilled in the art will readily recognize, however, that the universal clamp 600 may be appropriately coupled to any of the handles disclosed herein, and several variations thereof, without departing from the scope of the disclosure.

In one or more embodiments, the universal clamp 600 may include a locking plate 602 and an interface plate 604. Similar to the universal clamp 110 described above, a coupling post 136 may extend from the locking plate 602 and one or more indexing holes 140 may be defined in the locking plate 602. The coupling interaction between the coupling post 136 and the corresponding coupling aperture 132 (FIGS. 5a and 5b) of the handle 502 and the coupling interaction between the indexing holes 140 and corresponding indexing protrusions 134 of the handle 502 may be substantially similar as described above, and therefore will not be discussed again.

The universal clamp 600 may further include a first pivotable elongate extension 606a and a second pivotable elongate extension 606b. Each elongate extension 606a,b may be pivotably coupled to the interface plate 604 at corresponding first and second pivot points 608a and 608b, respectively. The pivotable nature of the pivotable elongate extensions 606a,b allows the use of a larger (e.g., longer) locking plate 602, which, in turn, allows the user to couple the universal clamp 600 to a wider (e.g., longer) transducer 102. Consequently, the universal clamp 600 may be coupled to a larger variety of sizes of transducers 102.

The pivotable elongate extensions 606a,b may be configured to extend through corresponding first and second apertures or slots (not shown) defined in the locking plate 602, and a mechanical securing device 610 may be secured to the end of each pivotable elongate extension 606a,b in order to prevent removal from the first and second apertures. In one embodiment, the mechanical securing devices 610 may be threaded devices, such as wing nuts, and configured to threadably engage corresponding threaded ends of each of the pivotable elongate extensions 606a,b. Accordingly, tightening the mechanical securing devices 610 may serve to more tightly secure the universal clamp 600 to a transducer 102 arranged between the locking plate 602 and the interface plate 604. As a result, the universal clamp 600 may be configured to be attached to a wide range of sizes and shapes of transducers 102, without departing from the scope of the disclosure.

Moreover, the universal clamp 600 may further include the adjustment screw 218 as described above with reference to FIG. 2. The threaded stem 222 may be extended through an adjustment aperture 224 defined in the interface plate 604 in order to finely adjust the position of the transducer 102 (not shown) with respect to the interface plate 604. Furthermore, the interior surfaces of each of the locking plate 602 and the interface plate 604 may have a layer of gripping material (not shown) applied thereto in order to provide increased frictional engagement with the transducer 102 during use. In at least one embodiment, the gripping material may be a thin layer of silicone rubber or another type of elastomer. In other embodiments, however, the gripping material may be made of other pliant or otherwise tacky materials such as, but not limited to, polymers, soft plastics, foams, textures, combinations thereof, or the like.

Therefore, the present invention is well adapted to attain the ends and advantages mentioned as well as those that are inherent therein. The particular embodiments disclosed above are illustrative only, as the present invention may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative embodiments disclosed above may be altered, combined, or modified and all such variations are considered within the scope and spirit of the present invention. The invention illustratively disclosed herein suitably may be practiced in the absence of any element that is not specifically disclosed herein and/or any optional element disclosed herein. While compositions and methods are described in terms of "comprising," "containing," or "including" various components or steps, the compositions and methods can also "consist essentially of" or "consist of" the various components and steps. All numbers and ranges disclosed above may vary by some amount. Whenever a numerical range with a lower limit and an upper limit is disclosed, any number and any included range falling within the range is specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values. Also, the terms in the claims have their plain, ordinary meaning unless otherwise explicitly and clearly defined by the patentee. Moreover, the indefinite articles "a" or "an," as used in the claims, are defined herein to mean one or more than one of the element that it introduces. If there is any conflict in the usages of a word or term in this specification and one or more patent or other documents that may be incorporated herein by reference, the definitions that are consistent with this specification should be adopted.

The invention claimed is:

1. A grip assembly, comprising:
   a locking plate defining first and second apertures and a coupling post extending from the locking plate;
   an interface plate having a first elongate extension being extendable at least partially through the first aperture and coupled thereto and a second elongate extension being extendable at least partially through the second aperture and coupled thereto; and
   a handle having a grip, a coupling interface, and a neck extending between the grip and the coupling interface, the coupling interface defining a coupling aperture for receiving the coupling post, whereby the handle is coupled to the locking plate.

2. The grip assembly of claim 1, wherein each elongate extension defines one or more apertures along their respective axial lengths.

3. The grip assembly of claim 2, wherein the locking plate comprises one or more locking mechanisms movably disposed within the locking plate and configured to extend through the one or more apertures to lock the first and second elongate extensions within the first and second apertures, respectively.

4. The grip assembly of claim 1, further comprising:
   one or more indexing protrusions that extend from the coupling interface; and
   one or more indexing holes arranged about the coupling post and being configured to receive the one or more indexing protrusions, thereby stabilizing the handle radially.

5. The grip assembly of claim 4, wherein the one or more indexing holes are circumferentially offset from each other at 90° intervals.

6. The grip assembly of claim 1, further comprising a magnet arranged on the coupling post and configured to magnetically-couple the handle to the locking plate.

7. The grip assembly of claim 1, wherein the first and second elongate extensions are pivotably coupled to the interface plate.

8. The grip assembly of claim 7, wherein the first and second elongate extensions extend through the first and second apertures, respectively, and are secured against removal therefrom with a mechanical securing device.

9. The grip assembly of claim 1, further comprising an adjustment screw extendable through an adjustment aperture defined in the interface plate, the adjustment screw being configured to bias a transducer arranged between the interface plate and the locking plate and thereby adjust a position of the transducer.

10. The grip assembly of claim 1, further comprising:
an attachment device defining an attachment device aperture; and
an attachment post extending from the coupling interface and receivable within the attachment device aperture, thereby coupling the attachment device to the handle.

11. The grip assembly of claim 10, wherein the attachment device is generally hemispherical.

12. A grip assembly, comprising:
a universal clamp including a slotted locking plate and an interface plate, the slotted locking plate defining first and second slots and the interface plate having a first elongate extension being extendable at least partially through the first slot and a second elongate extension being extendable at least partially through the second slot;
first and second locking mechanisms movably disposed within the locking plate and configured to lock the first and second elongate extensions within the first and second apertures, respectively;
a coupling post extending from the locking plate; and
a handle having a grip and a coupling interface defining a coupling aperture for receiving the coupling post, the coupling interface being configured to couple the handle to the universal clamp.

13. The grip assembly of claim 12, further comprising:
one or more indexing protrusions that extend from the coupling interface; and
one or more indexing holes arranged about the coupling post and being configured to receive the one or more indexing protrusions, thereby stabilizing the handle radially.

14. The grip assembly of claim 12, further comprising a magnet arranged on the coupling post and configured to magnetically-couple the handle to the locking plate.

\* \* \* \* \*